US009272966B2

(12) United States Patent
Kusakabe et al.

(10) Patent No.: US 9,272,966 B2
(45) Date of Patent: Mar. 1, 2016

(54) METHOD FOR PREPARING OPTICALLY ACTIVE 1-BROMO-1[3,5-BIS (TRIFLUOROMETHYL)PHENYL]ETHANE

(75) Inventors: Taichi Kusakabe, Chiba (JP); Kennosuke Matsuda, Tokyo (JP); Koichi Yamazaki, Tokyo (JP); Tadaaki Ohgiya, Saitama (JP); Kimiyuki Shibuya, Saitama (JP)

(73) Assignee: Kowa Company, Ltd., Aichi (JP)

( * ) Notice: Subject to any disclaimer, the term of this patent is extended or adjusted under 35 U.S.C. 154(b) by 77 days.

(21) Appl. No.: 13/811,651

(22) PCT Filed: Jul. 21, 2011

(86) PCT No.: PCT/JP2011/066512
§ 371 (c)(1),
(2), (4) Date: Apr. 11, 2013

(87) PCT Pub. No.: WO2012/011516
PCT Pub. Date: Jan. 26, 2012

(65) Prior Publication Data
US 2013/0190540 A1 Jul. 25, 2013

(30) Foreign Application Priority Data

Jul. 22, 2010 (JP) ................. 2010-164725
Jul. 22, 2010 (JP) ................. 2010-164726

(51) Int. Cl.
*C07C 22/08* (2006.01)
*C07C 22/04* (2006.01)
*C07C 17/16* (2006.01)
*C07C 17/04* (2006.01)
*C07B 53/00* (2006.01)

(52) U.S. Cl.
CPC .............. *C07C 17/04* (2013.01); *C07B 53/00* (2013.01); *C07C 17/16* (2013.01); *C07C 22/08* (2013.01); *C07B 2200/07* (2013.01)

(58) Field of Classification Search
CPC ........ C07C 17/16; C07C 22/04; C07C 17/093
See application file for complete search history.

(56) References Cited

U.S. PATENT DOCUMENTS 6,316,626 B1 * 11/2001 Swayze et al. ................. 546/207

FOREIGN PATENT DOCUMENTS

| CN | 101412711 A | 4/2009 | |
|---|---|---|---|
| JP | 2010077116 A | 4/2010 | |
| WO | WO 2008111604 A1 * | 9/2008 | |
| WO | WO-2009062371 A1 | 5/2009 | |
| WO | 2009/073777 A1 | 6/2009 | |
| WO | WO 2009073777 A1 * | 6/2009 | C07D 403/10 |
| WO | 2011/152508 A1 | 12/2011 | |
| WO | 2012/046681 A1 | 4/2012 | |

OTHER PUBLICATIONS

Kagechika, H. et al. J. Med. Chem. 1989, pp. 1098-1108.*
Aoki, T. et al. Patent No. WO2008111604A, Sep. 2008, pp. 1-60; English translation attached.*
Hutchins, R. O. et al. J. Org. Chem. 1976, 41, pp. 1071-1073.*
Thakur, V. V. et al. Indian J. Chem. 2005, 44B, pp. 557-562.*
Office Action issued for corresponding Chinese Patent Application No. 201180035700.9 issued on Mar. 12, 2014.
Karel M. J. Brands et al., "Efficient Synthesis of NK1 Receptor Antagonist Aprepitant Using a Crystallization-Induced Diastereoselective Transformation", Journal of the American Chemical Society, vol. 126, No. 8, pp. 2129-2135 (2003).
Jeffrey T. Kuethe et al., "Stereoselective Preparation of a Cyclopentane-Based NK1 Receptor Antagonist Bearing an Unsymmetrically Substituted Sec-Sec Ether", The Journal of Organic Chemistry, vol. 71, No. 19, pp. 7378-7390 (Sep. 15, 2006).
Chandrashekar R. Elati et al., "A convergent approach to the synthesis of aprepitant: a potent human NK-1 receptor antagonist", Tetrahedron Letters, vol. 48, pp. 8001-8004 (2007).
James Cason et al., "Investigation of Methods for Preparing Pure Secondary Alkyl Halides", The Journal of Organic Chemistry, vol. 26, No. 10, pp. 3645-3649 (Oct. 1961).
Vinay V. Thakur et al., "Enantioselective synthesis of (S)-α-arylpropionic acids via Pd-catalyzed kinetic resolution of benzylic alcohols", Indian Journal of Chemistry, vol. 44B, pp. 557-562 (Mar. 2005).
Gerhard Bringmann et al., "Improved Methods for Dehydration and Hydroxy/Halogen Exchange using Novel Combinations of Triphenylphosphine and Halogenated Ethanes", International Journal of Methods in Synthetic Organic Chemistry, No. 2, pp. 139-141 (Feb. 1983).
E. J. Corey et al., "A Method for Selective Conversion of Allylic and Benzylic Alcohols to Halides Under Neutral Conditions", Tetrahedron Letters, No. 42, pp. 4339-4342 (1972).
International Preliminary Report on Patentability (PCT/IB/373) in English (and copy in the original Japanese) for corresponding PCT/JP2011/066512 (mailed Feb. 21, 2013).
Official Action mailed on Jan. 27, 2015, in corresponding Japanese Patent Application No. 2012-525419 (along with English translation).
Perez-Prieto, Julia, et al., "Benzo[d]-1,2-oxaphospholes as precursors of stabilized C-centered radicals", Organic Letters, vol. 6, No. 4, p. 561-564, S1-2.
Official Action issued in corrersponding Chinese Patent Application 201180035700.9 with its English translation, Aug. 8, 2014, 19 pages.
Official Action issued in the corresponding Chinese Patent Application dated Feb. 16, 2015 and its English translation.
Official Action issued in the corresponding Chinese Patent Application dated Jun. 2, 2015 and its English translation.
European Search eport dated Oct. 8, 2015 in corresponding European Patent Application No. 11809686.6.

* cited by examiner

*Primary Examiner* — Fereydoun G Sajjadi
*Assistant Examiner* — Medhanit Bahta
(74) *Attorney, Agent, or Firm* — Mintz Levin Cohn Ferris Glovsky and Popeo, P.C.; Peter F. Corless

(57) ABSTRACT

A method for preparing optically active 1-bromo-1-[3,5-bis (trifluoromethyl)-phenyl]ethane having a high optical purity, which comprises the step of brominating optically active 1-[3,5-bis(trifluoromethyl)phenyl]ethanol by using, as a brominating agent, (a) a combination of a phosphorus halide and hydrogen bromide, (b) a combination of 1,2-dibromo-1,1,2, 2-tetrachloroethane and an organic phosphorous compound represented by the general formula (I): $P(R^1)(R^2)(R^3)$ (in the formula, $R^1$, $R^2$, and $R^3$ independently represent a $C_{6-10}$ aryl group, a $C_{6-10}$ aryloxy group, a $C_{1-10}$ alkyl group, a $C_{1-10}$ alkoxyl group, a $C_{3-6}$ cycloalkyl group, or a $C_{3-6}$ cycloalkoxy group), or (c) a combination of N-bromosuccinimide and a dialkyl sulfide.

20 Claims, No Drawings

METHOD FOR PREPARING OPTICALLY ACTIVE 1-BROMO-1[3,5-BIS(TRIFLUOROMETHYL)PHENYL]ETHANE

CROSS-REFERENCES TO RELATED APPLICATIONS

This application is a 35 U.S.C. §371 U.S. national entry of International Application PCT/JP2011/066512 (WO 2012/011516) having an International filing date of Jul. 21, 2011, which claims under 35 U.S.C. §119(a) the benefit of Japanese Application Nos. 2010-164725, filed Jul. 22, 2010 and 2010-164726, filed Jul. 22, 2010, the entire contents of which are incorporated herein by reference.

TECHNICAL FIELD

The present invention relates to a method for preparing optically active 1-bromo-1-[3,5-bis(trifluoromethyl)phenyl]ethane which is useful as a raw material for preparation of medicaments, agricultural chemicals, industrial products, and the like.

BACKGROUND ART

Optically active 1-[3,5-bis(trifluoromethyl)phenyl]ethyl group is important as an element unit of compounds useful as medicaments, agricultural chemicals, and the like, and 1-bromo-1-[3,5-bis(trifluoromethyl)phenyl]ethane is an extremely useful compound as a raw material for preparing compounds containing that group. For example, there has been disclosed use of 1-bromo-1-[3,5-bis(trifluoromethyl)-phenyl]ethane as a raw material for the preparation of compounds that act as an NK-1 receptor antagonist (Non-patent documents 1 and 2). However, although the compound has the aforementioned important usefulness, only a method for preparing racemate of 1-bromo-1-[3,5-bis(trifluoromethyl)phenyl]ethane has been known, and no publication is found that specifically reports a method for preparing optically active compound thereof.

Racemate of 1-bromo-1-[3,5-bis(trifluoromethyl)phenyl]ethane can be synthesized by the method shown in Scheme 1 mentioned below (Patent document 1). This method comprises the steps of converting 3,5-bis(trifluoromethyl)acetophenone into an alcohol compound by reduction with sodium borohydride in methanol, and brominating the resulting alcohol compound by using phosphorus tribromide in toluene.

Scheme 1

[Formula 1]

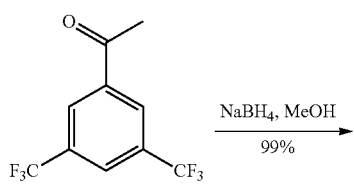

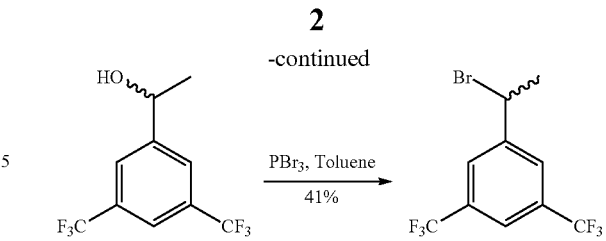

Racemate of 1-bromo-1-[3,5-bis(trifluoromethyl)phenyl]ethane can also be synthesized by the method shown in Scheme 2 mentioned below (Non-patent document 3). This method comprises the step of converting 3',5'-bis-(trifluoromethyl)acetophenone into an alcohol compound by reduction with sodium borohydride in methanol, and brominating this alcohol compound by a treatment with hydrobromic acid and sulfuric acid. However, Patent document 1 and Non-patent document 3 do not specifically disclose any method for preparing optically active 1-bromo-1-[3,5-bis(trifluoromethyl)phenyl]ethane.

Scheme 2

[Formula 2]

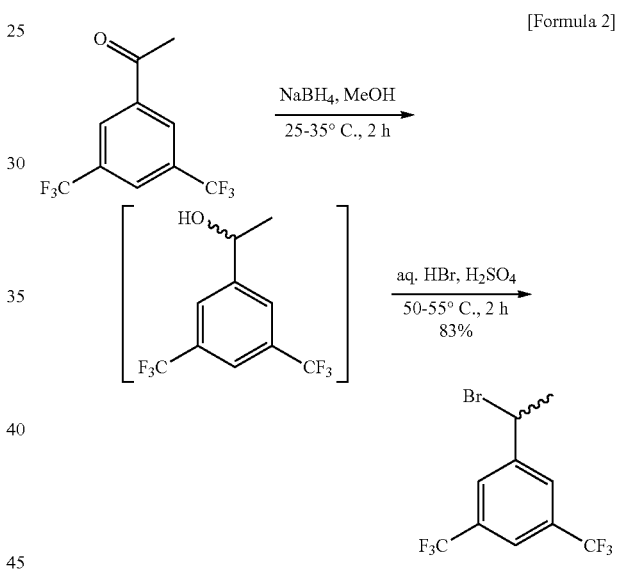

One of enantiomers of optically active 1-[3,5-bis(trifluoromethyl)phenyl]-ethanol with high optical purity can be obtained by subjecting bis-3',5'-(trifluoromethyl)phenylacetophenone to an asymmetric reduction reaction, or subjecting bis-3,5-(trifluoromethyl)benzaldehyde to an asymmetric methylation reaction. Therefore, if the alcohol of high optical purity as a starting material can be converted into 1-bromo-1-[3,5-bis(trifluoromethyl)phenyl]ethane with maintaining the high optical purity of the starting material, such a preparation method can be an industrially convenient and efficient preparation method. However, any method for efficiently preparing 1-bromo-1-[3,5-bis(trifluoromethyl)phenyl]ethane by using such an optically active alcohol as a starting material with maintaining high optical purity of the alcohol is not known so far.

As a general method for brominating hydroxyl group, there is known a method of converting hydroxyl group of an alkyl alcohol or benzyl alcohol into a leaving group such as sulfonic acid ester group, and brominating the result by a substitution reaction with bromide ion (Non-patent document 4). It has also been reported that if phosphorus tribromide is made to react with optically active 1-phenylethanol at low temperature in the presence of an excessive amount of pyridine in diethyl ether, 1-phenylbromoethane can be obtained in a high yield (conversion ratio, 93.9%; Non-patent document 5).

[Formula 3]

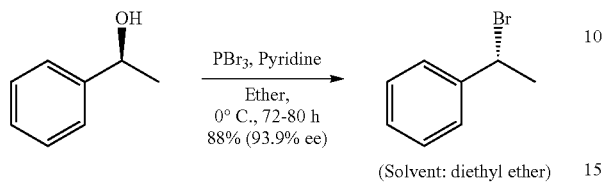

(Solvent: diethyl ether)

Further, there have also been reported a method of exchanging hydroxyl group for a halogen by using 1,2-dibromo-1,1,2,2-tetrachloroethane and triphenylphosphine (Non-patent document 6), and a method of exchanging hydroxyl group for a halogen by using N-bromosuccinimide and dimethyl sulfide (Non-patent document 7). However, it is not known so far that 1-bromo-1-[3,5-bis(trifluoromethyl) phenyl]ethane can be prepared by applying these methods to optically active 1-[3,5-bis(trifluoromethyl)phenyl]ethanol with maintaining high optical purity of the starting material.

[Formula 4]

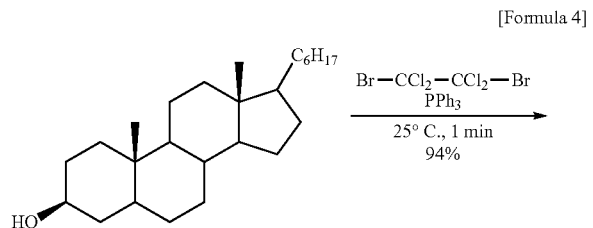

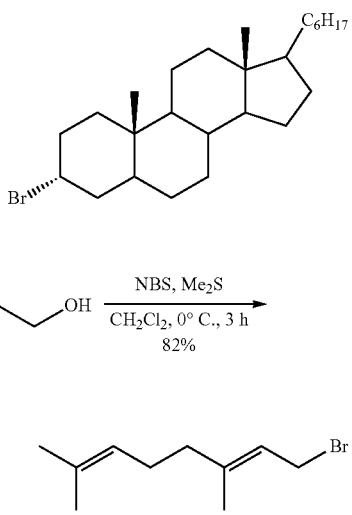

In addition, as a method for preparing an optically active compound, there is generally performed optical resolution of racemate by chiral column chromatography. However, since 1-bromo-1-[3,5-bis(trifluoromethyl)phenyl]ethane is highly reactive, a method utilizing optical resolution of racemate to provide an optical isomer may possibly be accompanied by decomposition and racemization of the objective substance, and it is expected that an optical isomer cannot be stably supplied. Also in Non-patent document 2 mentioned above, racemate of 1-bromo-1-[3,5-bis(trifluoromethyl)-phenyl] ethane is used as a raw material without any treatment, and there is employed a method of performing optical resolution of the resulting mixture of diastereomers in two steps to obtain the optically active objective substance.

[Formula 5]

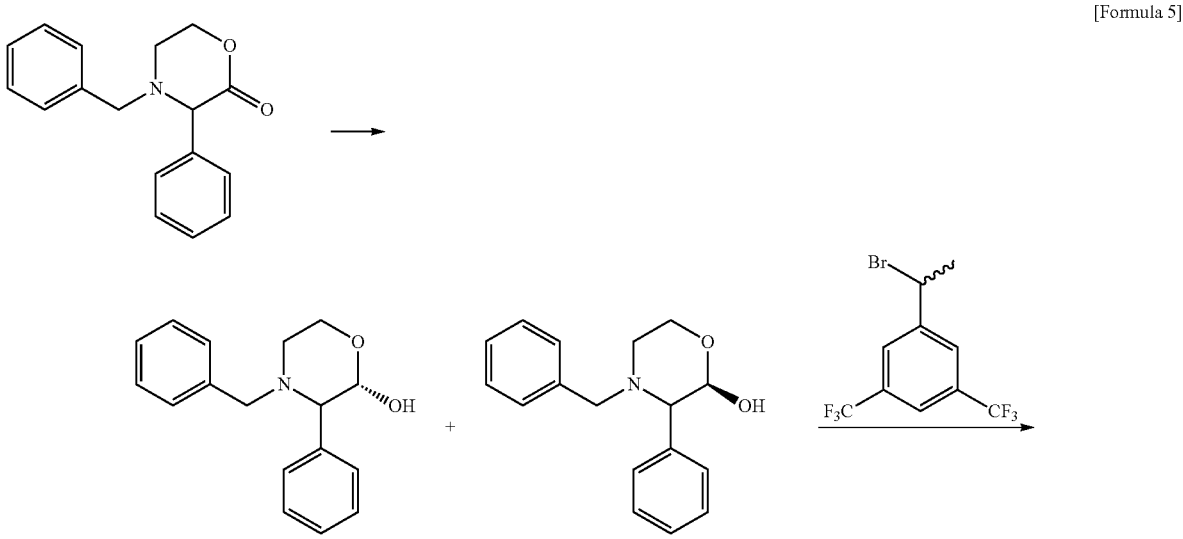

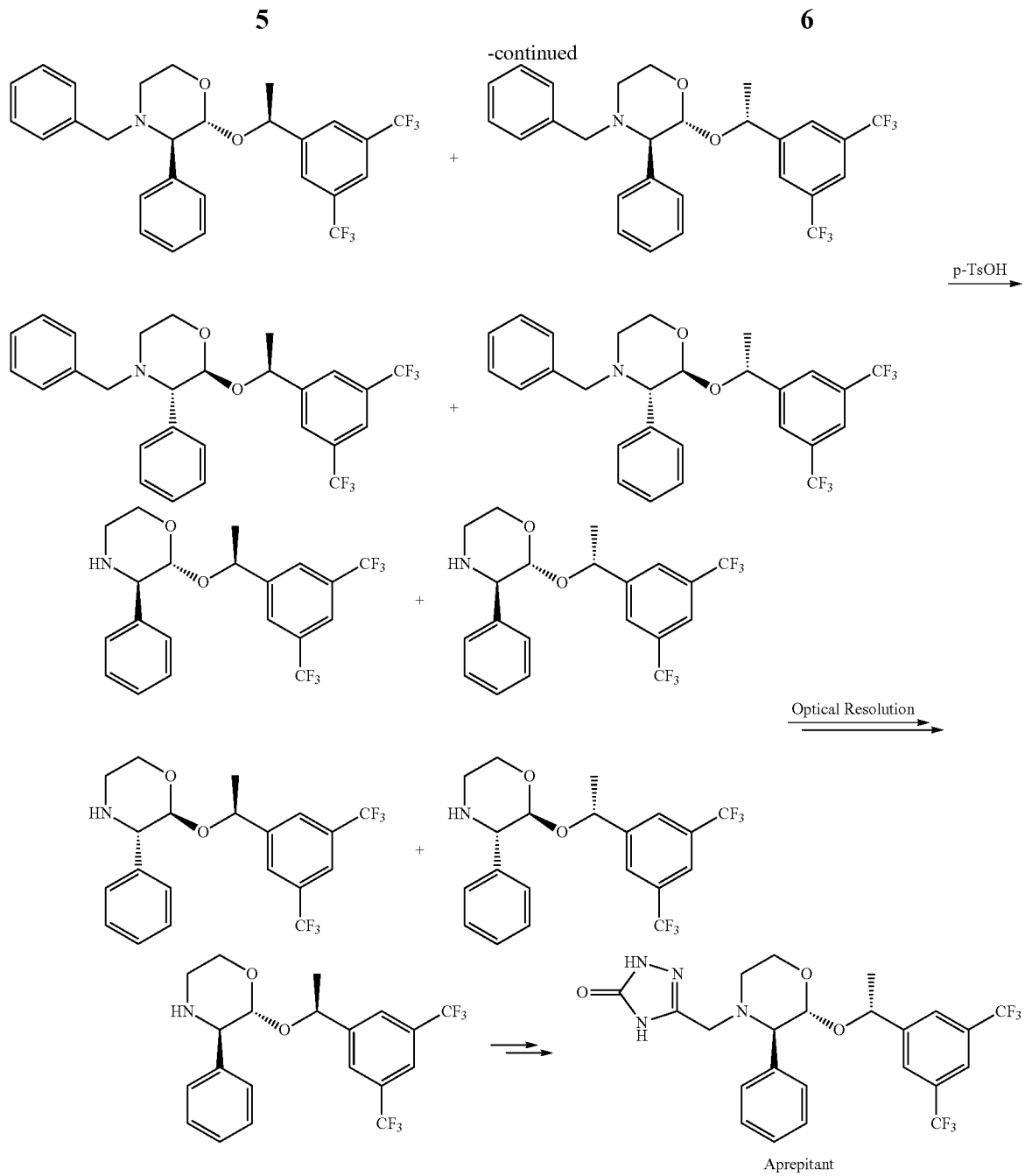

Aprepitant

PRIOR ART PUBLICATIONS

Patent Documents

Patent document 1: International Patent Publication WO2008/129951
Patent document 2: International Patent Publication WO2007/044829

Non-Patent Documents

Non-patent document 1: J. Am. Chem. Soc., 125, 2129-2135 (2003)
Non-patent document 2: J. Org. Chem., 71, 7378-7390 (2006)
Non-patent document 3: Tetrahedron Lett., 48, 8001-8004 (2007)
Non-patent document 4: J. Org. Chem., 26, 3645-3649 (1961)
Non-patent document 5: Indian J. Chem., Sec B, 44B, 557-562 (2005)
Non-patent document 6: Synthesis Commun., 139-141 (1983)
Non-patent document 7: Tetrahedron Lett., 42, 4339-4342 (1972)

SUMMARY OF THE INVENTION

Object to be Achieved by the Invention

An object of the present invention is to provide a method for efficiently preparing optically active 1-bromo-1-[3,5-bis(trifluoromethyl)phenyl]ethane in a high yield by using optically active 1-[3,5-bis(trifluoromethyl)phenyl]ethanol as a starting material while a high optical purity of the starting material is maintained.

Means for Achieving the Object

The inventors of the present invention conducted various researches to achieve the aforementioned object, and obtained a result that when the bromination method of Non-patent document 4 mentioned above is applied to optically active (R)-1-[3,5-bis(trifluoromethyl)phenyl]ethanol, a substitution/exchange reaction of bromine occurred between an already produced desired benzyl bromide and bromide ion existing in the reaction system, and thus almost complete racemization of the resulting 1-bromo-1-[3,5-bis(trifluoromethyl)phenyl]ethane proceeded (see, Comparative Example 1). Further, when a bromination reaction was performed for (R)-1-[3,5-bis(trifluoromethyl)phenyl]ethanol under the same conditions as those of Non-patent document 5 mentioned above, a result was obtained that the desired benzyl bromide was obtainable only in a low yield (refer to Comparative Example 2). It was considered that under these bromination conditions, the already produced desired benzyl bromide and bromide ions were allowed to coexist in the reaction system, and the objective substance further reacted with the bromide ions to generate racemate.

The inventors of the present invention further conducted researches, and found that if optically active 1-[3,5-bis(trifluoromethyl)phenyl]ethanol was brominated by using, as a brominating agent, (a) a combination of a phosphorus halide and a bromide, (b) a combination of 1,2-dibromo-1,1,2,2-tetrachloroethane and an organic phosphorous compound such as triphenylphosphine in the presence of a solvent, or (c) a combination of N-bromosuccinimide and a dialkyl sulfide in the presence of a solvent, the desired optically active 1-bromo-1-[3,5-bis(trifluoromethyl)phenyl]ethane with maintained high optical purity was successfully prepared.

The present invention thus provides a method for preparing optically active 1-bromo-1-[3,5-bis(trifluoromethyl)phenyl]ethane, which comprises the step of brominating optically active 1-[3,5-bis(trifluoromethyl)phenyl]ethanol by using, as a brominating agent, (a) a combination of a phosphorus halide and hydrogen bromide, (b) a combination of 1,2-dibromo-1,1,2,2-tetrachloroethane and an organic phosphorous compound represented by the general formula (I): $P(R^1)(R^2)(R^3)$ (in the formula, $R^1$, $R^2$, and $R^3$ independently represent a $C_{6-10}$ aryl group, a $C_{6-10}$ aryloxy group, a $C_{1-10}$ alkyl group, a $C_{1-10}$ alkoxyl group, a $C_{3-6}$ cycloalkyl group, or a $C_{3-6}$ cycloalkoxy group), or (c) a combination of N-bromosuccinimide and a dialkyl sulfide.

According to preferred embodiments of the aforementioned method, there are provided the aforementioned method, wherein the optically active 1-[3,5-bis(trifluoromethyl)phenyl]ethanol is (S)-1-[3,5-bis(trifluoromethyl)phenyl]ethanol, and the optically active 1-bromo-1-[3,5-bis(trifluoromethyl)phenyl]ethane is (R)-1-bromo-1-[3,5-bis(trifluoromethyl)phenyl]ethane; and the aforementioned method, wherein the optically active 1-[3,5-bis(trifluoromethyl)phenyl]ethanol is (R)-1-[3,5-bis(trifluoromethyl)phenyl]ethanol, and the optically active 1-bromo-1-[3,5-bis(trifluoromethyl)phenyl]ethane is (S)-1-bromo-1-[3,5-bis(trifluoromethyl)-phenyl]ethane.

According to preferred embodiments of the aforementioned method using the combination of (a), there are provided the aforementioned method, wherein the phosphorus halide is phosphorus tribromide; the aforementioned method, wherein hydrobromic acid is used as the hydrogen bromide; the aforementioned method, wherein a solution of hydrogen bromide in acetic acid is used as the hydrogen bromide; the aforementioned method, wherein phosphorus tribromide is used in an amount in the range of 0.4 to 0.6 equivalent based on the optically active 1-[3,5-bis(trifluoromethyl)phenyl]ethanol; the aforementioned method, wherein hydrogen bromide is used in an amount in the range of 0.8 to 1.2 equivalents based on the optically active 1-[3,5-bis(trifluoromethyl)phenyl]ethanol; the aforementioned method, which is performed in the absence of a solvent; the aforementioned method, wherein heptane is used as the solvent; and the aforementioned method, wherein reaction temperature is 10 to 15° C.

According to preferred embodiments of the aforementioned method using the combination of (b), there are provided the aforementioned method, wherein the reaction is performed in the presence of a solvent; the aforementioned method, wherein the organic phosphorous compound represented by the general formula (I) is triphenylphosphine; the aforementioned method, wherein 1,2-dibromo-1,1,2,2-tetrachloroethane is used in an amount in the range of 1.0 to 1.2 equivalents based on the optically active 1-[3,5-bis(trifluoromethyl)phenyl]ethanol; the aforementioned method, wherein triphenylphosphine is used in an amount in the range of 1.0 to 1.2 equivalents based on the optically active 1-[3,5-bis(trifluoromethyl)phenyl]ethanol; the aforementioned method, wherein the solvent is an aromatic hydrocarbon or a halogenated hydrocarbon; the aforementioned method, wherein the solvent is toluene, dichloromethane, or 1,2-dichloroethane; and the aforementioned method, wherein reaction temperature is 0 to 30° C.

According to preferred embodiments of the aforementioned method using the combination of (c), there are provided the aforementioned method, wherein the reaction is performed in the presence of a solvent; the aforementioned method, wherein the dialkyl sulfide is dimethyl sulfide; the aforementioned method, wherein N-bromosuccinimide is used in an amount in the range of 1.4 to 1.6 equivalents based on the optically active 1-[3,5-bis(trifluoromethyl)phenyl]ethanol; the aforementioned method, wherein dimethyl sulfide is used in an amount in the range of 1.7 to 1.9 equivalents based on the optically active 1-[3,5-bis(trifluoromethyl)phenyl]ethanol; the aforementioned method, wherein the solvent is a halogenated hydrocarbon; the aforementioned method, wherein the solvent is dichloromethane; and the aforementioned method, wherein reaction temperature is 0 to 30° C.

From another aspect, the present invention provides optically active 1-bromo-1-[3,5-bis(trifluoromethyl)phenyl]ethane. The present invention also provides optically active 1-bromo-1-[3,5-bis(trifluoromethyl)phenyl]ethane obtainable by the aforementioned preparation method. The optically active 1-bromo-1-[3,5-bis(trifluoromethyl)phenyl]ethane preferably has an optical purity of 97.0 to 99.5% ee.

Effect of the Invention

According to the method of the present invention, optically active 1-bromo-1-[3,5-bis(trifluoromethyl)phenyl]ethane useful as a raw material for preparation of medicaments, agricultural chemicals, industrial products and the like can be prepared from optically active 1-[3,5-bis(trifluoromethyl)phenyl]ethanol in a high yield by one step without using complicated operations while optical purity of the raw material is maintained.

MODES FOR CARRYING OUT THE INVENTION

The method of the present invention is for preparing optically active 1-bromo-1-[3,5-bis(trifluoromethyl)phenyl]

ethane, and the method is characterized by comprising the step of brominating optically active 1-[3,5-bis(trifluoromethyl)phenyl]-ethanol by using, as a brominating agent, (a) a combination of a phosphorus halide and hydrogen bromide, (b) a combination of 1,2-dibromo-1,1,2,2-tetrachloroethane and an organic phosphorous compound represented by the general formula (I): $P(R^1)(R^2)(R^3)$ (in the formula, $R^1$, $R^2$, and $R^3$ independently represent a $C_{6-10}$ aryl group, a $C_{6-10}$ aryloxy group, a $C_{1-10}$ alkyl group, a $C_{1-10}$ alkoxyl group, a $C_{3-6}$ cycloalkyl group, or a $C_{3-6}$ cycloalkoxy group), or (c) a combination of N-bromosuccinimide and a dialkyl sulfide. When a brominating agent consisting of the combination of (b) or (c) mentioned above is used, the reaction is preferably performed in the presence of a solvent.

Optically active 1-[3,5-bis(trifluoromethyl)phenyl]ethanol used as a raw material in the method of the present invention can be prepared by a known method such as the method of subjecting bis-3,5-(trifluoromethyl)phenyl methyl ketone to an asymmetric reduction reaction, or the method of subjecting bis-3,5-(trifluoromethyl)benzaldehyde to an asymmetric methylation reaction, and one of the enantiomers can be obtained at a high optical purity.

Hereafter, the method using the combination of (a) mentioned above will be explained in detail.

As the phosphorus halide, a phosphorus bromide such as phosphorus tribromide, phosphorus pentabromide, and phosphorus oxybromide can be used. However, phosphorus halides other than phosphorus bromide such as phosphorus trichloride, phosphorus pentachloride, and phosphorus oxychloride can also be used. Two or more kinds of phosphorus halides may be used in combination. Among them, a phosphorus bromide is preferred, and phosphorus tribromide is particularly preferred. As hydrogen bromide, hydrobromic acid, a solution of hydrogen bromide in acetic acid, for example, a 30% solution in acetic acid, and the like can be used. As the combination of a phosphorus halide and hydrogen bromide, a combination of phosphorus tribromide and a solution of hydrogen bromide in acetic acid is preferred.

The phosphorus halide such as phosphorus tribromide can be used in an amount in the range of, for example, 0.5 to 2.0 equivalents, preferably 0.4 to 0.6 equivalent, based on the raw material alcohol. Hydrogen bromide can be used in an amount in the range of, for example, 0.7 to 3.0 equivalents, preferably 0.8 to 1.2 equivalents, based on the raw material alcohol.

The aforementioned reaction can be performed in the presence or absence of a solvent. When the reaction is performed in the presence of a solvent, type of the solvent to be used is not particularly limited so long that the solvent does not participate in the reaction. Examples of the solvent include, for example, aromatic hydrocarbons such as benzene, toluene, xylene, mesitylene, chlorobenzene, 1,2-dichlorobenzene, and nitrobenzene; aliphatic hydrocarbons such as n-pentane, n-hexane, cyclohexane, n-heptane, n-octane, and n-decane; halogenated hydrocarbons such as dichloromethane, 1,2-dichloroethane, chloroform, and carbon tetrachloride, and the like. Benzene, toluene, xylene, dichloromethane, 1,2-dichloroethane, n-pentane, n-hexane, and n-heptane can be preferably used, and n-heptane can be more preferably used. These solvents can be used alone or in combination, and amount of the solvent used is not particularly limited.

Although the reaction temperature is not particularly limited, the reaction may be usually performed in the range of −50 to 150° C., preferably −20 to 80° C., most preferably 0 to 15° C. The reaction time is usually preferably 5 minutes to 48 hours, more preferably 30 minutes to 36 hours, most preferably 12 to 24 hours.

After completion of the reaction, the reaction system can be subjected to ordinary post-treatments to obtain a crude product. The resulting crude product can be subjected to a purification operation such as activated charcoal treatment, distillation, and column chromatography as required to obtain optically active 1-bromo-1-[3,5-bis(trifluoromethyl) phenyl]ethane at high chemical purity and optical purity. Optical purity of the optically active 1-bromo-1-[3,5-bis(trifluoromethyl)phenyl]ethane is, for example, 95% ee or higher, preferably 96% ee or higher, but not particularly limited.

The phosphorus halide such as phosphorus tribromide and hydrogen bromide such as hydrobromic acid used in the method using the combination of (a) mentioned above are used for the general bromination reactions, and they are widely used reagents also suitable for industrial scale production, as used in the manufacture of kainic acid, pentoxyverine citrate, fosfestrol, betahistine mesilate, and the like (Guide Book of Japanese Pharmacopoeia, 13th Edition, 1996, Hirokawa Publishing Co.). Therefore, the method of the present invention is suitable for industrial application.

Hereafter, the method using the combination of (b) mentioned above will be explained in detail.

As for the organic phosphorous compound represented by the general formula (I), examples of the $C_{6-10}$ aryl group include, for example, phenyl group, naphthyl group, azulenyl group, and the like. Examples of the $C_{6-10}$ aryloxy group include, for example, phenoxy group, naphthyloxy group, azulenyloxy group, and the like. Examples of the $C_{1-10}$ alkyl group include, for example, methyl group, ethyl group, n-propyl group, isopropyl group, n-butyl group, s-butyl group, isobutyl group, t-butyl group, pentyl group, hexyl group, octyl group, nonyl group, decyl group, and the like. Examples of the $C_{1-10}$ alkoxyl group include, for example, methoxy group, ethoxy group, n-propoxy group, isopropoxy group, n-butoxy group, s-butoxy group, isobutoxy group, t-butoxy group, pentoxy group, hexyloxy group, octyloxy group, nonyloxy group, decyloxy group, and the like. Examples of the $C_{3-6}$ cycloalkyl group include, for example, cyclopropyl group, cyclobutyl group, cyclopentyl group, cyclohexyl group, and the like. Examples of the $C_{3-6}$ cycloalkoxy group include, for example, cyclopropoxy group, cyclobutoxy group, cyclopentyloxy group, cyclohexyloxy group, and the like.

As for the organic phosphorous compound represented by the general formula (I), it is preferred that $R^1$, $R^2$, and $R^3$ are $C_{6-10}$ aryl groups, and it is more preferred that $R^1$, $R^2$, and $R^3$ are phenyl groups, i.e., the organic phosphorous compound is triphenylphosphine.

1,2-Dibromo-1,1,2,2-tetrachloroethane can be used in an amount in the range of 1.0 to 3.0 equivalents, preferably 1.0 to 1.2 equivalents, based on the raw material alcohol. The organic phosphorous compound represented by the general formula (I), for example, triphenylphosphine, can be used in an amount in the range of, for example, 1.0 to 3.0 equivalents, preferably 1.0 to 1.2 equivalents, based on the raw material alcohol.

The aforementioned reaction can be preferably performed in the presence of a solvent. When the reaction is performed in the presence of a solvent, type of the solvent to be used is not particularly limited so long that the solvent does not participate in the reaction. Examples of the solvent include, for example, aromatic hydrocarbons such as benzene, toluene, xylene, mesitylene, chlorobenzene, 1,2-dichlorobenzene, and nitrobenzene; aliphatic hydrocarbons such as n-pentane, n-hexane, cyclohexane, n-heptane, n-octane, and n-decane; halogenated hydrocarbons such as dichloromethane, 1,2-dichloroethane, chloroform, and carbon tetrachloride, and the like. Among them, benzene, toluene, xylene, dichloromethane, and 1,2-dichloroethane are preferred, and toluene, dichloromethane, and 1,2-dichloroethane are more preferred. These solvents can be used alone or in combination, and the amount of the solvent used is not particularly limited.

Although the reaction temperature is not particularly limited, the reaction may be usually performed in the range of −50 to 150° C., preferably −20 to 80° C., most preferably 0 to 30° C. The reaction time is usually preferably 5 minutes to 48 hours, more preferably 30 minutes to 36 hours, most preferably 1 to 12 hours.

After completion of the reaction, the reaction system can be subjected to ordinary post-treatments to obtain a crude product. The resulting crude product can be subjected to a purification operation such as activated charcoal treatment, distillation, and column chromatography as required to obtain optically active 1-bromo-1-[3,5-bis(trifluoromethyl) phenyl]ethane at high chemical purity and optical purity. Optical purity of the optically active 1-bromo-1-[3,5-bis(trifluoromethyl)phenyl]ethane is, for example, 95% ee or higher, preferably 96% ee or higher, but not particularly limited.

Hereafter, the method using the combination of (c) mentioned above will be explained in detail.

Although two of the alkyl groups in the dialkyl sulfide may be the same or different, they are preferably the same. Examples of the alkyl group include the aforementioned $C_{1-10}$ alkyl group, for example, methyl group, ethyl group, n-propyl group, isopropyl group, n-butyl group, s-butyl group, isobutyl group, t-butyl group, pentyl group, hexyl group, octyl group, nonyl group, decyl group, and the like. Methyl groups can be preferably used as two of the alkyl groups.

N-Bromosuccinimide can be used in an amount in the range of, for example, 1.0 to 3.0 equivalents, preferably 1.0 to 1.8 equivalents, more preferably 1.4 to 1.6 equivalents, based on the raw material alcohol. The dialkyl sulfide, for example, dimethyl sulfide, can be used in an amount in the range of, for example, 1.0 to 3.0 equivalents, preferably 1.5 to 2.0 equivalents, more preferably 1.7 to 1.9 equivalents, based on the raw material alcohol.

The aforementioned reaction can be preferably performed in the presence of a solvent. When the reaction is performed in the presence of a solvent, type of the solvent to be used is not particularly limited so long that the solvent does not participate in the reaction. Examples of the solvent include, for example, aromatic hydrocarbons such as benzene, toluene, xylene, mesitylene, chlorobenzene, 1,2-dichlorobenzene, and nitrobenzene; aliphatic hydrocarbons such as n-pentane, n-hexane, cyclohexane, n-heptane, n-octane, and n-decane; halogenated hydrocarbons such as dichloromethane, 1,2-dichloroethane, chloroform, and carbon tetrachloride, and the like. Among them, benzene, toluene, xylene, dichloromethane, and 1,2-dichloroethane are preferred, and toluene, dichloromethane, and 1,2-dichloroethane are more preferred. These solvents can be used independently or in combination, and the amount of the solvent used is not particularly limited.

Although the reaction temperature is not particularly limited, the reaction may be usually performed in the range of −50 to 150° C., preferably −20 to 80° C., most preferably 0 to 30° C. The reaction time is usually preferably 5 minutes to 48 hours, more preferably 30 minutes to 36 hours, most preferably 1 to 12 hours.

After completion of the reaction, the reaction system can be subjected to usual post-treatments to obtain a crude product. The resulting crude product can be subjected to a purification operation such as activated charcoal treatment, distillation, and column chromatography as required to obtain optically active 1-bromo-1-[3,5-bis(trifluoromethyl)phenyl] ethane at high chemical purity and optical purity. Optical purity of the optically active 1-bromo-1-[3,5-bis(trifluoromethyl)phenyl]ethane is, for example, 95% ee or higher, preferably 96% ee or higher, but not particularly limited.

EXAMPLES

Hereafter, the present invention will be still more specifically explained with reference to examples. However, the scope of the present invention is not limited by these examples.

The absolute configuration of 1-bromo-1-[3,5-bis(trifluoromethyl)phenyl]-ethane shown in Example 1 mentioned below was determined by converting the compound into α-[3,5-bis(trifluoromethyl)phenyl]ethylamine, and comparing sign of the specific rotation thereof with that of the commercially available same compound of which absolute configuration was known, as shown in Examples 1-4 and 1-5. Further, optical purity of the desired 1-bromo-1-[3,5-bis(trifluoromethyl)phenyl]ethane was determined by chiral HPLC analysis (CHIRALPAK (registered trademark) AS-RH; mobile phase, ethanol/water=60/40; flow rate, 0.5 mL/minute; column temperature, 25° C.; detection wavelength, 220 nm; retention time, first peak/(R) 21.8 minutes, second peak/(S) 26.0 minutes).

As (S)-1-[3,5-bis(trifluoromethyl)phenyl]ethanol, (S)-1-[3,5-bis(trifluoromethyl)phenyl]ethanol having an optical purity of 99.5% or 98% was used. As for the products, optical purities (% ee) as well as numerical values of "conversion ratio (%)" representing relative ratio of maintained optical purity (conversion ratio (%)=% ee of product/% ee of raw material alcohol) are shown.

Example 1-1

Under an argon atmosphere, (S)-1-[3,5-bis(trifluoromethyl)phenyl]ethanol (1.0 g, 3.87 mmol, >99.5% ee) was added dropwise with phosphorus tribromide (0.52 g, 1.94 mmol) on a water bath at a temperature lower than 20° C., and the mixture was stirred at 19 to 22° C. for 30 minutes. The reaction mixture was cooled, and added dropwise with hydrogen bromide (30% solution in acetic acid, 0.76 mL, 3.87 mmol) at a temperature lower than 0° C., and the mixture was stirred at 13 to 15° C. for 18 hours. The reaction mixture was poured into ice water, and the mixture was extracted with n-hexane (15 mL×2). The organic layers were combined, washed with saturated aqueous sodium hydrogencarbonate (15 mL×1) and then with saturated brine (15 mL×1), dried over anhydrous sodium sulfate, and then concentrated under reduced pressure. The resulting crude product was purified by column chromatography (silica gel, 8 g; developing solvent, n-hexane) to obtain 1.06 g of (R)-1-bromo-1-[3,5-bis(trifluoromethyl)phenyl]ethane as colorless oil.

Yield: 85%

Chiral HPLC analysis: optical purity, 96.8% ee (first peak); conversion ratio, 97.3% $[\alpha]_D^{25}$=+56.6 (c=1.18, $CHCl_3$)

¹H-NMR (CDCl₃): δ 2.08 (3H, d, J=7.1 Hz), 5.21 (1H, q, J=7.1 Hz), 7.81 (1H, s), 7.87 (2H, s).

Example 1-2

Under an argon atmosphere, (R)-1-[3,5-bis(trifluoromethyl)phenyl]ethanol (1.0 g, 3.87 mmol, >99.5% ee) was added dropwise with phosphorus tribromide (0.52 g, 1.94 mmol) on a water bath at a temperature lower than 20° C., and the mixture was stirred at 19 to 22° C. for 30 minutes. The reaction mixture was cooled, and added dropwise with hydrogen bromide (30% solution in acetic acid, 0.76 mL, 3.87 mmol) at a temperature lower than 0° C., and the mixture was stirred at 13 to 15° C. for 18 hours. The reaction mixture was poured into ice water, and the mixture was extracted with n-hexane (15 mL×2). The organic layers were combined, washed with saturated aqueous sodium hydrogencarbonate (15 mL×1) and then with saturated brine (15 mL×1), dried over anhydrous sodium sulfate, and then concentrated under reduced pressure. The resulting crude product was purified by column chromatography (silica gel, 8 g; developing solvent, n-hexane) to obtain 1.13 g of (S)-1-bromo-1-[3,5-bis(trifluoromethyl)phenyl]ethane as colorless oil.

Yield: 91%

Chiral HPLC analysis: optical purity, 96.3% ee (second peak); conversion ratio, >96.8%

$[\alpha]_D^{25}$=−55.6 (c=1.23, CHCl₃)

The ¹H-NMR spectrum was the same as that shown in Example 1-1.

Example 1-3

Under an argon atmosphere, a suspension of (S)-1-[3,5-bis(trifluoromethyl)-phenyl]ethanol (1.0 g, 3.87 mmol, >99.5% ee) in heptane (2 mL) was added dropwise with phosphorus tribromide (0.52 g, 1.94 mmol) at 0 to 5° C., and the mixture was stirred at 0 to 5° C. for 30 minutes. The reaction mixture was added dropwise with hydrogen bromide (30% solution in acetic acid, 0.76 mL, 3.87 mmol) at 0 to 5° C., and the mixture was stirred at 10° C. for 17 hours. The reaction mixture was poured into ice water, and the mixture was extracted with n-hexane (15 mL×2). The organic layers were combined, washed with saturated aqueous sodium hydrogencarbonate (15 mL×1) and then with saturated brine (15 mL×1), dried over anhydrous sodium sulfate, and then concentrated under reduced pressure. The resulting crude product was purified by column chromatography (silica gel, 8 g; developing solvent, n-hexane) to obtain 1.12 g of (R)-1-bromo-1-[3,5-bis(trifluoromethyl)phenyl]ethane as colorless oil.

Yield: 90%

Chiral HPLC analysis: optical purity, 97.7% ee (second peak); conversion ratio, 98.2%

The ¹H-NMR spectrum was the same as that shown in Example 1-1.

Example 1-4

A solution of 1-bromo-1-[3,5-bis(trifluoromethyl)phenyl]ethane obtained in Example 1-1 (first peak, 96.8% ee; 102 mg; 0.32 mmol) in dimethylformamide (1 mL) was added with sodium azide (62.0 mg, 0.95 mmol), and the mixture was stirred at −18 to −15° C. for 3 hours. The reaction solution was diluted with ethyl acetate/hexane (1:1), and the organic layer was washed with water and saturated brine, dried over anhydrous sodium sulfate, and then concentrated under reduced pressure to obtain 118.8 mg of a crude product of 1-azido-[3,5-bis(trifluoromethyl)phenyl]ethane.

¹H-NMR (CDCl₃): δ 1.61 (3H, d, J=6.8 Hz), 4.79 (1H, q, J=6.8 Hz), 7.78 (2H, s), 7.84 (1H, s).

Example 1-5

The crude product of 1-azido-[3,5-bis(trifluoromethyl)phenyl]ethane obtained in Example 1-4 was added with palladium-fibroin (18 mg) and methanol (6 mL), and after the atmosphere was replaced with hydrogen, the mixture was stirred at room temperature. After stirring over 1 hour, the reaction mixture was filtered through Celite, and concentrated, and the resulting residue was purified by silica gel column chromatography (chloroform:methanol=50:1 to 5:1) to obtain 58.9 mg of α-[3,5-bis(trifluoromethyl)phenyl]ethylamine as colorless oil.

Yield: 74% (for two steps)

$[\alpha]_D^{25}$=−15.4 (c=1.01, CHCl₃)

¹H-NMR (CDCl₃): δ 1.42 (3H, d, J=6.8 Hz), 1.58 (2H, br-s), 4.30 (1H, q, J=6.8 Hz), 7.75 (1H, s), 7.85 (2H, s).

Standard sample: (S)-α-[3,5-bis(trifluoromethyl)phenyl]ethylamine produced by Central Glass Co., Ltd.

Lot. 0102000

Optical purity, 99% ee $[\alpha]_D^{25}$=−15.9 (c=1.15, CHCl₃)

The sign of the specific optical rotation of the product was compared with that of the marketed standard sample amine, and it was found that α-[3,5-bis(trifluoromethyl)phenyl]ethylamine obtained in Example 1-5 was S-isomer. This amine was obtained from 1-bromo-1-[3,5-bis(trifluoromethyl)phenyl]ethane via the nucleophilic substitution of azide ion, and accordingly, it was confirmed that 1-bromo-1-[3,5-bis(trifluoromethyl)phenyl]ethane obtained in Example 1-1 was R-isomer (chiral HPLC analysis, first peak).

Bromination reaction using phosphorus tribromide was performed under the conditions shown in Table 1 in the same manner as that used in Examples 1-1 and 1-2. Isolation yields, optical purities (% ee), and conversion ratios (% ee of product/% ee of raw material) are shown in Table 1.

TABLE 1

| No. | Starting material (% ee, steric configuration) | Brominating agent (Equivalent) | Additive (Equivalent) | Solvent (fold amount) | Starting reaction temperature and reaction time | Reaction temperature and reaction time after addition | Yield (%) | % ee/conversion ratio |
|---|---|---|---|---|---|---|---|---|
| 1 | 99.5 (S) | PBr₃ (0.5) | HBr/AcOH (1.0) | neat | rt, 0.5 h | 13 to 15° C., 18 h | 85 | 96.8/97.3 |
| 2 | 99.5 (R) | PBr₃ (0.5) | HBr/AcOH (1.0) | neat | rt, 0.5 h | 13 to 15° C., 18 h | 91 | 96.3/96.8 |
| 3 | 99.5 (S) | PBr₃ (0.5) | HBr/AcOH (1.0) | Heptane (2) | 0° C., 0.5 h | 10° C., 17 h | 90 | 97.7/98.2 |
| 4 | 99.5 (R) | PBr₃ (1.0) | H₂O | neat | rt, 0.5 h | rt, 0.5 h | 44 | 99.3/99.8 |
| 5 | 99.5 (R) | PBr₃ (1.0) | HBr aq. (0.7) | neat | rt, 0.5 h | rt, 15 h | 44 | 99.3/99.8 |
| 6 | 99.5 (R) | PBr₃ (1.0) | HBr/AcOH (1.0) | neat | rt, 0.5 h | rt, 1 h | 69 | 97.1/97.6 |

TABLE 1-continued

| No. | Starting material (% ee, steric configuration) | Brominating agent (Equivalent) | Additive (Equivalent) | Solvent (fold amount) | Starting reaction temperature and reaction time | Reaction temperature and reaction time after addition | Yield (%) | % ee/conversion ratio |
|---|---|---|---|---|---|---|---|---|
| 7 | 99.5 (R) | PBr₃ (1.0) | HBr/AcOH (1.0) | neat | rt, 0.5 h | rt, 15 h | 87 | 95.0/95.5 |
| 8 | 99.5 (R) | PBr₃ (1.0) | HBr/AcOH (1.0) | neat | rt, 0.5 h | 5° C., 15 h | 74 | 97.6/98.1 |
| 9 | 99.5 (R) | PBr₃ (1.0) | HBr/AcOH (3.0) | neat | rt, 0.5 h | rt, 1 h | 74 | 96.3/96.8 |
| 10 | 99.5 (R) | PBr₃ (1.0) | HBr/AcOH (3.0) | neat | rt, 0.5 h | rt, 15 h | 86 | 53.7/54.2 |
| 11 | 99.5 (R) | PBr₃ (1.0) | HBr/AcOH (3.0) | neat | rt, 0.5 h | 5° C., 15 h | 79 | 96.7/97.2 |
| 12 | 99.5 (R) | PBr₃ (1.0) | HBr/AcOH (10.0) | neat | rt, 0.5 h | rt, 1 h | 75 | 94.7/95.2 |
| 13 | 99.5 (R) | PBr₃ (1.0) | HBr/AcOH (10.0) | neat | rt, 0.5 h | rt, 15 h | 87 | 21.1/21.2 |
| 14 | 99.5 (R) | PBr₃ (0.5) | HBr/AcOH (1.0) | neat | rt, 0.5 h | rt, 1 h | 73 | 97.1/97.6 |
| 15 | 99.5 (R) | PBr₃ (0.5) | HBr/AcOH (1.0) | neat | rt, 0.5 h | rt, 15 h | 90 | 92.2/92.7 |
| 16 | 99.5 (R) | PBr₃ (0.5) | HBr/AcOH (1.0) | neat | rt, 0.5 h | 5° C., 15 h | 73 | 98.1/98.6 |
| 17 | 98 (S) | PBr₃ (0.5) | HBr/AcOH (1.0) | neat | rt, 0.5 h | −20 to −15° C., 18 h | 52 | 99.2/99.0 |
| 18 | 98 (S) | PBr₃ (0.5) | HBr/AcOH (1.0) | neat | rt, 0.5 h | 0° C., 18 h | 61 | 99.0/99.0 |
| 19 | 98 (S) | PBr₃ (0.5) | HBr/AcOH (1.0) | neat | rt, 0.5 h | 22 to 25° C., 18 h | 88 | 95.3/97.2 |
| 20 | 99.5 (R) | PBr₃ (1.5) | HBr/AcOH (1.0) | DCM (2) | rt, 0.5 h | rt, 15 h | 55 | 95.3/95.8 |
| 21 | 99.5 (S) | PBr₃ (0.5) | HBr/AcOH (1.0) | Heptane (2) | 0° C., 0.5 h | 5° C., 17 h | 77 | 98.2/98.7 |
| 22 | 99.5 (S) | PBr₃ (0.5) | HBr/AcOH (1.0) | Heptane (2) | 0° C., 0.5 h | 15° C., 22 h | 92 | 97.1/97.6 |
| 23 | 99.5 (R) | PBr₃ (1.1), Pyr (2.7) | | Et₂O (10) | −15° C., 2 h | −5° C., 48 h | 14 | Not measured |
| 24 | 99.5 (R) | PBr₃ (1.1), Pyr (2.7) | | Toluene (10) | −15° C., 2 h | −5° C., 48 h | trace | Not measured |
| 25 | 99.5 (R) | PBr₃ (1.1), Pyr (2.7) | | DCM (10) | −15° C., 2 h | −5° C., 48 h | 8 | Not measured |

Notes:
DCM, dichloromethane;
Pyr, pyridine

As clearly understood from the results shown in Table 1, the objective substance was successfully obtained in an extremely high yield with maintained high optical purity especially under the reaction conditions of Nos. 1 to 3 and 22.

The absolute configurations of 1-bromo-1-[3,5-bis(trifluoromethyl)phenyl]-ethane shown in Examples 2 mentioned below were determined by converting the compound into α-[3,5-bis(trifluoromethyl)phenyl]ethylamine, and comparing sign of the specific rotation thereof with that of the commercially available same compound of which absolute configuration was known, as shown in Examples 2-5 and 2-6. Further, optical purity of the desired 1-bromo-1-[3,5-bis(trifluoromethyl)phenyl]ethane was determined by chiral HPLC analysis (CHIRALPAK (registered trademark) AS-RH; mobile phase, ethanol/water=60/40; flow rate, 0.5 mL/minute; column temperature, 25° C.; detection wavelength, 220 nm; retention time, first peak/(R) 21.8 minutes, second peak/(S) 26.0 minutes).

As (S)-1-[3,5-bis(trifluoromethyl)phenyl]ethanol, (S)-1-[3,5-bis(trifluoromethyl)phenyl]ethanol having an optical purity of 99.5% or 98% was used. As for the products, optical purities (% ee) as well as numerical values of "conversion ratio (%)" representing relative ratio of maintained optical purity (conversion ratio (%)=% ee of product/% ee of raw material alcohol) are shown.

Example 2-1

Under an argon atmosphere, 1,2-dibromo-1,1,2,2-tetrachloroethane (7.57 g, 23.2 mmol) was dissolved in toluene (12.5 mL), the solution was added with triphenylphosphine (6.1 g, 23.2 mmol) at 0° C., and the mixture was stirred for 30 minutes. The reaction mixture was added dropwise with a solution of (S)-1-[3,5-bis(trifluoromethyl)phenyl]ethanol (5.0 g, 19.4 mmol, >99.5% ee) in toluene (12.5 mL) at 0° C. over 10 minutes or more, and then the mixture was warmed to room temperature, and stirred at the same temperature for 1 hour. The reaction mixture was added with n-hexane (25 mL), and the mixture was filtered through Celite. The filtrate was washed successively with water, saturated aqueous sodium hydrogencarbonate, and saturated brine, dried over sodium sulfate, and evaporated under reduced pressure. The resulting residue was distilled under reduced pressure (56° C., 0.7 mmHg) to obtain 5.52 g of (R)-1-bromo-1-[3,5-bis(trifluoromethyl)phenyl]ethane as colorless oil.

Yield: 89%

Chiral HPLC analysis: optical purity, >99.5% ee (first peak); conversion ratio, >99.5%

$[\alpha]_D^{25}$=+59.1 (c=1.03, CHCl₃)

¹H-NMR (CDCl₃): δ 2.08 (3H, d, J=7.1 Hz), 5.21 (1H, q, J=7.1 Hz), 7.81 (1H, s), 7.87 (2H, s).

Example 2-2

Under an argon atmosphere, 1,2-dibromo-1,1,2,2-tetrachloroethane (7.57 g, 23.2 mmol) was dissolved in toluene (12.5 mL), the solution was added with triphenylphosphine (6.1 g, 23.2 mmol) at 0° C., and the mixture was stirred for 30 minutes. The reaction mixture was added dropwise with a solution of (R)-1-[3,5-bis(trifluoromethyl)phenyl]ethanol (5.0 g, 19.4 mmol, >99.5% ee) in toluene (12.5 mL) at 0° C. over 10 minutes or more, and then the mixture was warmed to room temperature, and stirred at the same temperature for 1 hour. The reaction mixture was added with n-hexane (25 mL), and the mixture was filtered through Celite. The filtrate was washed successively with water, saturated aqueous sodium hydrogencarbonate, and saturated brine, dried over sodium sulfate, and evaporated under reduced pressure. The resulting residue was distilled under reduced pressure (56° C., 0.7 mmHg) to obtain 5.45 g of (S)-1-bromo-1-[3,5-bis(trifluoromethyl)phenyl]ethane as colorless oil.

Yield: 88%

Chiral HPLC analysis: optical purity, >99.0% ee (second peak); conversion ratio, >99.5%

The ¹H-NMR spectrum was the same as that shown in Example 2-1.

Example 2-3

Under an argon atmosphere, a suspension of N-bromosuccinimide (206 mg, 1.16 mmol) in anhydrous dichloromethane (3.8 mL) was added dropwise with dimethyl sulfide (105 μL, 1.40 mmol) under ice cooling over 3 minutes. The mixture was added dropwise with a solution of (S)-1-[3,5-bis(trifluoromethyl)phenyl]ethanol (200 mg, 0.78 mmol, >99.5% ee) in anhydrous dichloromethane (2 mL) at −20° C., and the mixture was stirred at room temperature for 9 hours. The reaction mixture was add with n-hexane, and the organic layer was washed with water and saturated brine, dried over anhydrous sodium sulfate, and then concentrated under reduced pressure. The resulting residue was purified by silica gel column chromatography (developing solvent, n-hexane) to obtain 144 mg of (R)-1-bromo-1-[3,5-bis(trifluoromethyl)phenyl]ethane as colorless oil.

Yield: 58%

Chiral HPLC analysis: optical purity, >99.5% ee (first peak); conversion ratio, >99.5%

The ¹H-NMR spectrum was the same as that shown in Example 2-1.

Example 2-4

Under an argon atmosphere, a suspension of N-bromosuccinimide (103 mg, 0.58 mmol) in anhydrous dichloromethane (2.0 mL) was added dropwise with dimethyl sulfide (53 μL, 0.70 mmol) under ice cooling over 3 minutes. The mixture was added dropwise with a solution of (R)-1-[3,5-bis(trifluoromethyl)phenyl]ethanol (100 mg, 0.39 mmol, >99.5% ee) in anhydrous dichloromethane (1 mL) at −20° C., and the mixture was stirred at room temperature for 6 hours. The reaction mixture was add with n-hexane, and the organic layer was washed with water and saturated brine, dried over anhydrous sodium sulfate, and then concentrated under reduced pressure. The resulting residue was purified by silica gel column chromatography (developing solvent, n-hexane) to obtain 82 mg of (S)-1-bromo-1-[3,5-bis(trifluoromethyl)phenyl]ethane as colorless oil.

Yield: 66%

Chiral HPLC analysis: optical purity, >99.5% ee (second peak); conversion ratio, >99.5%

The ¹H-NMR spectrum was the same as that shown in Example 2-1.

Example 2-5

A solution of 1-bromo-1-[3,5-bis(trifluoromethyl)phenyl]ethane obtained in Example 2-1 (first peak, 99.5% ee; 106 mg; 0.33 mmol) in dimethylformamide (1 mL) was added with sodium azide (64.4 mg, 0.99 mmol), and the mixture was stirred at −18 to −15° C. for 4 hours. The reaction solution was diluted with ethyl acetate/hexane (1:1), and the organic layer was washed with water and saturated brine, dried over anhydrous sodium sulfate, and then concentrated under reduced pressure to obtain 111.5 mg of a crude product of 1-azido-[3,5-bis(trifluoromethyl)phenyl]ethane.

¹H-NMR (CDCl₃): δ 1.61 (3H, d, J=6.8 Hz), 4.79 (1H, q, J=6.8 Hz), 7.78 (2H, s), 7.84 (1H, s).

Example 2-6

The crude product of 1-azido-[3,5-bis(trifluoromethyl)phenyl]ethane obtained in Example 2-5 was added with palladium-fibroin (18 mg) and methanol (6 mL), and after the atmosphere was replaced with hydrogen, the mixture was stirred at room temperature. After stirring over 1 hour, the reaction mixture was filtered through Celite, and concentrated, and the resulting residue was purified by silica gel column chromatography (chloroform:methanol=50:1 to 5:1) to obtain 77.6 mg of α-[3,5-bis(trifluoromethyl)phenyl]ethylamine as colorless oil.

Yield: 91% (for two steps)

$[\alpha]_D^{25} = -15.9$ (c=1.31, CHCl₃)

¹H-NMR (CDCl₃): δ 1.42 (3H, d, J=6.8 Hz), 1.58 (2H, br-s), 4.30 (1H, q, J=6.8 Hz), 7.75 (1H, s), 7.85 (2H, s).

Standard sample: (S)-α-[3,5-bis(trifluoromethyl)phenyl]ethylamine prepared by Central Glass Co., Ltd.

Lot. 0102000

Optical purity, 99% ee $[\alpha]_D^{25} = -15.9$ (c=1.15, CHCl₃)

The sign of the specific rotation of the product was compared with that of the marketed standard sample amine, and it was found that α-[3,5-bis(trifluoromethyl)-phenyl]ethylamine obtained in Example 2-6 was S-isomer. Thus, since this amine was obtained from 1-bromo-1-[3,5-bis(trifluoromethyl)phenyl]ethane via the nucleophilic substitution of azide ion, it was confirmed that 1-bromo-1-[3,5-bis(trifluoromethyl)-phenyl]ethane obtained in Example 2-1 was R-isomer (chiral HPLC analysis, first peak).

Reaction was performed under the bromination conditions shown in Table 2 in the same manner as that used in Examples 2-1 and 2-2. Isolation yields, optical purities (% ee), and conversion ratios (% ee of product/% ee of raw material) are shown in Table 2.

TABLE 2

| No. | Starting material (% ee, steric configuration) | Brominating agent (Equivalent) | Solvent | Reaction conditions | Yield (%) | % ee/conversion ratio |
| --- | --- | --- | --- | --- | --- | --- |
| 1 | 99.5 (S) | (CCl₂Br)₂ (1.2), PPh₃ (1.2) | Toluene | rt, 1 h | 89 | 99.5/99.9 |
| 2 | 99.5 (R) | (CCl₂Br)₂ (1.2), PPh₃ (1.2) | Toluene | Rt, 1 h | 88 | 99.5/99.9 |
| 3 | 99.5 (S) | NBS (1.5), Me₂S (1.8) | DCM | rt, 6 h | 58 | 99.5/99.9 |
| 4 | 99.5 (R) | NBS (1.5), Me₂S (1.8) | DCM | rt, 6 h | 66 | 99.5/99.9 |
| 5 | 99.5 (R) | (CCl₂Br)₂ (1.0), PPh₃ (1.0) | DCM | 0° C., 1 h | 79 | 99.5/99.9 |
| 6 | 99.5 (R) | (CCl₂Br)₂ (1.5), PPh₃ (1.5) | DCM | 0° C., 0.5 h | 89 | 86.2/86.6 |
| 7 | 99.5 (R) | (CCl₂Br)₂ (2.0), PPh₃ (2.0) | DCM | 0° C., 0.5 h | 92 | 97.6/98.1 |

TABLE 2-continued

| No. | Starting material (% ee, steric configuration) | Brominating agent (Equivalent) | Solvent | Reaction conditions | Yield (%) | % ee/conversion ratio |
|---|---|---|---|---|---|---|
| 8 | 99.5 (R) | (CCl$_2$Br)$_2$ (2.0), PPh$_3$ (2.0) | 1,2-DCE | rt, 1 h | 92 | 67.3/67.6 |
| 9 | 99.5 (R) | (CCl$_2$Br)$_2$ (1.1), PPh$_3$ (1.1) | 1,2-DCE | 0° C., 0.5 h | 79 | 92.9/93.4 |
| 10 | 99.5 (R) | (CCl$_2$Br)$_2$ (1.1), PPh$_3$ (1.1) | Toluene | rt, 1 h | 81 | 99.0/99.5 |
| 11 | 99.5 (R) | NBS (1.0), Me$_2$S (1.0) | DCM | rt, 19 h | 47 | 99.3/99.8 |
| 12 | 99.5 (R) | NBS (1.2), Me$_2$S (1.2) | DCM | rt, 19 h | 64 | 98.9/99.4 |
| 13 | 99.5 (R) | NBS (1.0), PPh$_3$ (1.0) | DCM | rt, 20 h | 59 | 44.6/44.8 |
| 14 | 99.5 (R) | NBS (1.2), PPh$_3$ (1.2) | DCM | rt, 20 h | 71 | 3.9/3.9 |
| 15 | 99.5 (R) | NBS (1.5), PPh$_3$ (1.5) | DCM | rt, 1 h | 82 | 81.1/81.5 |
| 16 | 99.5 (R) | NBS (2.0), PPh$_3$ (2.0) | DCM | rt, 1 h | 89 | 68.4/68.7 |
| 17 | 99.5 (R) | NBS (1.5), PPh$_3$ (1.5) | Toluene | rt, 2 h | 56 | 98.7/99.2 |
| 18 | 99.5 (R) | NBS (1.5), PPh$_3$ (1.5) | THF | rt, 2 h | 72 | 47.5/47.7 |
| 19 | 99.5 (R) | NBS (1.5), PPh$_3$ (1.5) | DMF | rt, 1 h | 66 | 12.4/12.5 |
| 20 | 99.5 (R) | CBr$_4$ (1.2), PPh$_3$ (1.2) | DCM | 0° C. to rt, 1.5 h | 76 | 78.3/78.7 |
| 21 | 99.5 (R) | CBr$_4$ (1.2), PPh$_3$ (1.2) | Toluene | 0° C. to rt, 16 h | 65 | 85.7/86.1 |
| 22 | 99.5 (R) | CBr$_4$(1.2), PPh$_3$ (1.2) | THF | 0° C. to rt, 2.5 h | 75 | 87.8/88.2 |
| 23 | 99.5 (R) | Br$_2$ (1.5), PPh$_3$ (1.5) | DCM | 0° C., 0.5 h | 79 | 98.2/98.7 |
| 24 | 99.5 (R) | Br$_2$ (1.5), PPh$_3$ (1.5) | DCM | rt, 0.5 h | 79 | 67.5/67.8 |
| 25 | 99.5 (R) | Br$_2$ (1.2), PPh$_3$ (1.2) | DCM | 0° C., 2.5 h | 52 | 95.2/95.7 |
| 26 | 99.5 (R) | Br$_2$ (1.5), Me$_2$S (1.5) | DCM | rt, 24 h | complex mixture | |
| 27 | 99.5 (S) | LiBr (2.0), TMSCl (2.0) | CH$_3$CN | reflux, 20 h | 11 | 0 |
| 28 | 99.5 (S) | PyHBr$_3$ (1.2), HMDS (1.25) | CHCl$_3$ | 50° C., 20 h | complex mixture | |
| 29 | 99.5 (S) | DEAD (3.0), PPh$_3$ (3.0), ZnBr$_2$ (1.0) | THF | rt, 20 h | trace | |

Notes:
DCM, dichloromethane;
1,2-DCE, 1,2-dichloroethane;
NBS, N-bromosuccinimide;
THF, tetrahydrofuran;
DMF, N,N-dimethylformamide;
TMSCl, trimethylsilyl chloride;
PyHBr$_3$, pyridinium tribromide;
HMDS, 1,1,1,2,2,2-hexamethyldisilane;
DEAD, diethyl azodicarboxylate As clearly understood from the results shown in Table 2, the objective substance was successfully obtained in an extremely high yield with maintained high optical purity especially under the reaction conditions of Nos. 1 to 4.

Example 3

Comparative Example

With reference to Japanese Patent No. 3938651, a solution of (R)-1-[3,5-bis(trifluoromethyl)phenyl]ethanol (optical purity, >99.5% ee; 1.6 g; 6.20 mmol) in dichloromethane (20 mL) was added with methanesulfonyl chloride (0.58 mL, 7.44 mmol), triethylamine (1.30 mL, 9.3 mmol), and dimethylaminopyridine (76 mg, 0.62 mmol) with stirring under ice cooling, and the mixture was stirred at the same temperature for 30 minutes. The reaction mixture was added with 1 N hydrochloric acid and chloroform at the same temperature, and the organic layer was separated. The aqueous layer was extracted with chloroform (20 mL×3), and the organic layers were combined, washed with saturated brine, then dried over anhydrous sodium sulfate, and concentrated under reduced pressure to obtain (R)-methanesulfonic acid 1-[3,5-bis(trifluoromethyl)phenyl]ethyl ester (2.23 g) as colorless oil. Then, a solution of the resulting (R)-methanesulfonic acid 1-[3,5-bis(trifluoromethyl)phenyl]ethyl ester (2.23 g) in N,N-dimethylformamide (20 mL) was added with sodium bromide (1.26 g, 12.25 mmol), and the mixture was stirred at 50° C. for 1 hour. The reaction mixture was added with water (30 mL) at room temperature, and the mixture was extracted with hexane (30 mL×3). The organic layer was washed with saturated brine, dried over anhydrous sodium sulfate, and then concentrated under reduced pressure. The resulting residue was purified by silica gel column chromatography (hexane:ethyl acetate=10:1) to obtain 1.85 g of 1-bromo-1-[3,5-bis(trifluoromethyl)phenyl]ethane as colorless oil. On the basis of the specific rotation, it was confirmed that the resulting 1-bromo-1-[3,5-bis(trifluoromethyl)phenyl]ethane was obtained after racemization.

Yield: 93% (for two steps)

$[\alpha]_D^{25}$=−0.19 (c=1.01, CHCl$_3$)

The $^1$H-NMR spectrum was the same as that shown in Example 1-1.

Example 4

Comparative Example

A solution of (R)-1-[3,5-bis(trifluoromethyl)phenyl]ethanol (optical purity, >99.5% ee; 100 mg; 0.39 mmol) in dehydrated diethyl ether (1.0 mL) was added with dehydrated pyridine (69.4 mg, 0.89 mmol) under an argon atmosphere. The mixture was slowly added dropwise with a solution of phosphorus tribromide (117.2 mg, 0.43 mmol) in dehydrated diethyl ether (0.5 mL) at −15 to −20° C., and the mixture was stirred at the same temperature for 2 hours, and then left standing at −5° C. for 48 hours. Then, the reaction mixture was added with cooled water (3 mL) under ice cooling, and the mixture was stirred at room temperature for 15 minutes, and then extracted with diethyl ether (10 mL). The organic layer was concentrated under reduced pressure, and the resulting residue was purified by silica gel column chromatography (silica gel, 3.0 g; developing solvent, n-hexane) to obtain 17.6 mg of 1-bromo-1-[3,5-bis(trifluoromethyl)phenyl]ethane as colorless oil.

Yield: 14%

The $^1$H-NMR spectrum was the same as that shown in Example 1-1.

INDUSTRIAL APPLICABILITY

By the method of the present invention, optically active 1-bromo-1-[3,5-bis(trifluoromethyl)phenyl]ethane useful as a raw material for preparation of medicaments, agricultural chemicals, industrial products, and the like can be efficiently prepared in a high yield under industrially applicable conditions.

What is claimed is:

1. Optically active 1-bromo-1-[3,5-bis(trifluoromethyl)phenyl]ethane wherein the optically active 1-bromo-1-[3,5-bis(trifluoromethyl)phenyl]ethane is (R)-1-bromo-1-[3,5-bis(trifluoromethyl)phenyl]ethane or (S)-1-bromo-1-[3,5-bis(trifluoromethyl)phenyl]ethane.

2. The optically active 1-bromo-1-[3,5-bis(trifluoromethyl)phenyl]ethane according to claim 1, which has an optical purity of 97.0 to 99.5% ee.

3. A method for preparing optically active 1-bromo-1-[3,5-bis(trifluoromethyl)-phenyl]ethane, which comprises the step of brominating optically active 1-[3,5-bis(trifluoromethyl)phenyl]ethanol by using, as a brominating agent, (a) a combination of a phosphorus halide and hydrogen bromide, (b) a combination of 1,2-dibromo-1,1,2,2-tetrachloroethane and an organic phosphorous compound represented by the general formula (I): $P(R^1)(R^2)(R^3)$ (in the formula, $R^1$, $R^2$, and $R^3$ independently represent a $C_{6-10}$ aryl group, a $C_{6-10}$ aryloxy group, a $C_{1-10}$ alkyl group, a $C_{1-10}$ alkoxyl group, a $C_{3-6}$ cycloalkyl group, or a $C_{3-6}$ cycloalkoxy group), or (c) a combination of N-bromosuccinimide and a dialkyl sulfide,
    wherein an optical purity of the optically active 1-[3,5-bis(trifluoromethyl)phenyl]ethanol is maintained in the optically active 1-bromo-1-[3,5-bis(trifluoromethyl)-phenyl]ethane after brominating, wherein the optically active 1-bromo-1-[3,5-bis(trifluoromethyl)-phenyl]ethane is (R)-1-bromo-1-[3,5-bis(trifluoromethyl)phenyl]ethane or (S)-1-bromo-1-[3,5-bis(trifluoromethyl)phenyl]ethane having an optical purity of 97.0 to 99.5% ee, and
    wherein the phosphorus halide is phosphorus tribromide.

4. The method according to claim 3, wherein the optically active 1-[3,5-bis(trifluoromethyl)phenyl]ethanol is (S)-1-[3,5-bis(trifluoromethyl)phenyl]ethanol, and the optically active 1-bromo-1-[3,5-bis(trifluoromethyl)phenyl]ethane is (R)-1-bromo-1-[3,5-bis(trifluoromethyl)phenyl]ethane.

5. The method according to claim 3, wherein the optically active 1-[3,5-bis(trifluoromethyl)phenyl]ethanol is (R)-1-[3,5-bis(trifluoromethyl)phenyl]ethanol, and the optically active 1-bromo-1-[3,5-bis(trifluoromethyl)phenyl]ethane is (S)-1-bromo-1-[3,5-bis(trifluoromethyl)phenyl]ethane.

6. The method according to claim 5, wherein bromination is performed by using the combination of (b) or (c) in the presence of a solvent, and the solvent is an aromatic hydrocarbon or a halogenated hydrocarbon.

7. The method according to claim 6, wherein the solvent is toluene, dichloromethane, or 1,2-dichloroethane.

8. The method according to claim 6, wherein the organic phosphorous compound represented by the general formula (I) is triphenylphosphine.

9. A method for preparing optically active 1-bromo-1-[3,5-bis(trifluoromethyl)-phenyl]ethane, which comprises the step of brominating optically active 1-[3,5-bis(trifluoromethyl)phenyl]ethanol by using, as a brominating agent, (a) a combination of a phosphorus halide and hydrogen bromide, (b) a combination of 1,2-dibromo-1,1,2,2-tetrachloroethane and an organic phosphorous compound represented by the general formula (I): $P(R^1)(R^2)(R^3)$ (in the formula, $R^1$, $R^2$, and $R^3$ independently represent a $C_{6-10}$ aryl group, a $C_{6-10}$ aryloxy group, a $C_{1-10}$ alkyl group, a $C_{1-10}$ alkoxyl group, a $C_{3-6}$ cycloalkyl group, or a $C_{3-6}$ cycloalkoxy group), or (c) a combination of N-bromosuccinimide and a dialkyl sulfide,
    wherein an optical purity of the optically active 1-[3,5-bis(trifluoromethyl)phenyl]ethanol is maintained in the optically active 1-bromo-1-[3,5-bis(trifluoromethyl)-phenyl]ethane after brominating, wherein the optically active 1-bromo-1-[3,5-bis(trifluoromethyl)-phenyl]ethane is (R)-1-bromo-1-[3,5-bis(trifluoromethyl)phenyl]ethane or (S)-1-bromo-1-[3,5-bis(trifluoromethyl)phenyl]ethane having an optical purity of 97.0 to 99.5% ee, and
    wherein hydrobromic acid or a solution of hydrogen bromide in acetic acid is used as the hydrogen bromide.

10. The method according to claim 9, wherein the optically active 1-[3,5-bis(trifluoromethyl)phenyl]ethanol is (S)-1-[3,5-bis(trifluoromethyl)phenyl]ethanol, and the optically active 1-bromo-1-[3,5-bis(trifluoromethyl)phenyl]ethane is (R)-1-bromo-1-[3,5-bis(trifluoromethyl)phenyl]ethane.

11. The method according to claim 9, wherein the optically active 1-[3,5-bis(trifluoromethyl)phenyl]ethanol is (R)-1-[3,5-bis(trifluoromethyl)phenyl]ethanol, and the optically active 1-bromo-1-[3,5-bis(trifluoromethyl)phenyl]ethane is (S)-1-bromo-1-[3,5-bis(trifluoromethyl)phenyl]ethane.

12. The method according to claim 9, wherein bromination is performed by using the combination of (b) or (c) in the presence of a solvent and the solvent is an aromatic hydrocarbon or a halogenated hydrocarbon.

13. The method according to claim 12, wherein the solvent is toluene, dichloromethane, or 1,2-dichloroethane.

14. The method according to claim 12, wherein the organic phosphorous compound represented by the general formula (I) is triphenylphosphine.

15. A method for preparing optically active 1-bromo-1-[3,5-bis(trifluoromethyl)-phenyl]ethane, which comprises the step of brominating optically active 1-[3,5-bis(trifluoromethyl)phenyl]ethanol by using, as a brominating agent, (a) a combination of a phosphorus halide and hydrogen bromide, (b) a combination of 1,2-dibromo-1,1,2,2-tetrachloroethane and an organic phosphorous compound represented by the general formula (I): $P(R^1)(R^2)(R^3)$ (in the formula, $R^1$, $R^2$, and $R^3$ independently represent a $C_{6-10}$ aryl group, a $C_{6-10}$ aryloxy group, a $C_{1-10}$ alkyl group, a $C_{1-10}$ alkoxyl group, a $C_{3-6}$ cycloalkyl group, or a $C_{3-6}$ cycloalkoxy group), or (c) a combination of N-bromosuccinimide and a dialkyl sulfide,
    wherein an optical purity of the optically active 1-[3,5-bis(trifluoromethyl)phenyl]ethanol is maintained in the optically active 1-bromo-1-[3,5-bis(trifluoromethyl)-phenyl]ethane after brominating, wherein the optically active 1-bromo-1-[3,5-bis(trifluoromethyl)-phenyl]ethane is (R)-1-bromo-1-[3,5-bis(trifluoromethyl)phenyl]ethane or (S)-1-bromo-1-[3,5-bis(trifluoromethyl)phenyl]ethane having an optical purity of 97.0 to 99.5% ee, and wherein the reaction is performed in the presence of heptane.

16. The method according to claim 15, wherein the optically active 1-[3,5-bis(trifluoromethyl)phenyl]ethanol is (S)-1-[3,5-bis(trifluoromethyl)phenyl]ethanol, and the optically active 1-bromo-1-[3,5-bis(trifluoromethyl)phenyl]ethane is (R)-1-bromo-1-[3,5-bis(trifluoromethyl)phenyl]ethane.

17. The method according to claim 15, wherein the optically active 1-[3,5-bis(trifluoromethyl)phenyl]ethanol is (R)-1-[3,5-bis(trifluoromethyl)phenyl]ethanol, and the optically active 1-bromo-1-[3,5-bis(trifluoromethyl)phenyl]ethane is (S)-1-bromo-1-[3,5-bis(trifluoromethyl)phenyl]ethane.

18. A method for preparing optically active 1-bromo-1-[3,5-bis(trifluoromethyl)-phenyl]ethane, which comprises the step of brominating optically active 1-[3,5-bis(trifluoromethyl)phenyl]ethanol by using, as a brominating agent, (a) a combination of a phosphorus halide and hydrogen bromide, (b) a combination of 1,2-dibromo-1,1,2,2-tetrachloroethane and an organic phosphorous compound represented by the general formula (I): $P(R^1)(R^2)(R^3)$ (in the formula, $R^1$, $R^2$, and $R^3$ independently represent a $C_{6-10}$ aryl group, a $C_{6-10}$ aryloxy group, a $C_{1-10}$ alkyl group, a $C_{1-10}$ alkoxyl group, a $C_{3-6}$ cycloalkyl group, or a $C_{3-6}$ cycloalkoxy group), or (c) a combination of N-bromosuccinimide and a dialkyl sulfide, wherein an optical purity of the optically active 1-[3,5-bis(trifluoromethyl)phenyl]ethanol is maintained in the optically active 1-bromo-1-[3,5-bis(trifluoromethyl)-phenyl]ethane after brominating, wherein the optically active 1-bromo-1-[3,5-bis(trifluoromethyl)-phenyl]ethane is (R)-1-bromo-1-[3,5-bis(trifluoromethyl)phenyl]ethane or (S)-1-bromo-1-[3,5-bis(trifluoromethyl)phenyl]ethane having an optical purity of 97.0 to 99.5% ee, and wherein bromination is performed by using the combination of (b) or (c) in the presence of a solvent, and wherein the dialkyl sulfide is dimethyl sulfide.

19. The method according to claim 18, wherein the optically active 1-[3,5-bis(trifluoromethyl)phenyl]ethanol is (S)-1-[3,5-bis(trifluoromethyl)phenyl]ethanol, and the optically active 1-bromo-1-[3,5-bis(trifluoromethyl)phenyl]ethane is (R)-1-bromo-1-[3,5-bis(trifluoromethyl)phenyl]ethane.

20. The method according to claim 18, wherein the optically active 1-[3,5-bis(trifluoromethyl)phenyl]ethanol is (R)-1-[3,5-bis(trifluoromethyl)phenyl]ethanol, and the optically active 1-bromo-1-[3,5-bis(trifluoromethyl)phenyl]ethane is (S)-1-bromo-1-[3,5-bis(trifluoromethyl)phenyl]ethane.

* * * * *